United States Patent [19]

Dietze et al.

[11] 4,146,613

[45] Mar. 27, 1979

[54] ORAL ANTI-DIABETIC DRUG COMPOSITION

[75] Inventors: Günther Dietze; Matthias Wicklmayr, both of Munich, Fed. Rep. of Germany

[73] Assignee: THERA Gesellschaft für Patentverwertung mbH, Fed. Rep. of Germany

[21] Appl. No.: 861,369

[22] Filed: Dec. 16, 1977

[30] Foreign Application Priority Data

Dec. 17, 1976 [DE] Fed. Rep. of Germany ....... 2657382

[51] Int. Cl.$^2$ .............................................. A61K 37/00
[52] U.S. Cl. .................................................. 424/177
[58] Field of Search ........................................ 424/177

[56] References Cited

PUBLICATIONS

"Arzneimittel", vol. I, Pharmakodynamica, Velag Chemie 1968, pp. 896–908.
"Diabetologie in Klinik und Praxis", (G. Thieme, Stuttgart (1974) pp. 18–23.
Frey, et al., "Klinische Wochenschrift" 1932, pp. 846–849.
Elmer et al., "Klinische Wochenschrift," 1932, pp. 1993–1995.

*Primary Examiner*—Delbert R. Phillips
*Attorney, Agent, or Firm*—Burns, Doane, Swecker & Mathis

[57] ABSTRACT

There is provided an anti-diabetic drug to be taken orally. This drug comprises a sulfonyl urea and a kinin in retarded form. The kinin may be a Brady kinin or kallidin and is used in retarded form in an amount of from about 10μ grams to about 20 milligrams per unit dosage.

10 Claims, No Drawings

ORAL ANTI-DIABETIC DRUG COMPOSITION

BACKGROUND OF THE INVENTION

1. Field of the Invention

This invention relates generally to drug compositions. More particularly, this invention relates to antidiabetic drug compositions which may be taken orally.

2. Description of the Prior Art

The human as well as other animal organisms need insulin, the pancreas hormone, in order to utilize the glucoses. Insulin stimulates the movement of the glucose from the blood into the tissue cells, especially the muscular cells, and expedites the synthesis of fats as well as of proteins in practically all organs. In diabetics, the pancreas will not produce this hormone in sufficient quantities, with the result that the glucose level in the blood rises, causing the known symptoms of diabetes mellitus. Thus, it becomes necessary to supply the diabetic with the required amount of this hormone by parenteral, that is subcutaneous, injections of insulin of other origin in order to maintain the sugar content of the blood at a normal or at least permissible level. Such injections require strict control and individual treatment of the respective patient.

Specific sulfonyl ureas which may be administered orally, are known to possess a blood sugar reducing effect because of their ability to stimulate insufficient insulin secretion in adult diabetics, and especially in those cases were diabetes occurs during old age. In this connection, see "Arzneimittel," Volume 1, Pharmakodynamica, Verlag Chemie 1968, pp. 896 to 908. However, sulfonyl ureas may have side effects, such as gastro-intestinal disturbances, toxic depressions of the bone marrow, widespread exanthemata and the like, depending on the dosage. In this connection, see Mehnert et al, "Diabetologie in Klinik und Praxis," [G. Thieme, Stuttgart (1974) ], pp. 18 to 23. In such instances it is necessary to reduce the dosage, possibly resulting in a rise of the blood sugar level above that which is permissible.

It is also known that an enzyme called "kallikrein" (German) is also produced by the pancreas and has a proteolytic effect. In this connection, see Frey et al, "Klinische Wochenschrift" (1932), pp. 846 to 849. In addition to its vasodilatoric and blood-pressure reducing effects, this enzyme also has the ability to lower slightly the blood sugar, and it is stated that this effect will occur even if the enzyme is applied orally. In this study it was also found that after administering the substance for several days, for example after three days, the effect would diminish or disappear. Thus, there was detected a tachyphylaxy, delimiting the therapeutic usefulness of this substance. The blood-sugar-reducing effect has not been confirmed by any other source. In this connection, see Elmer et al, "Klinische Wochenschrift," (1932), pp. 1993 to 1995.

For these reasons neither the kallikrein nor the so-called kinins (which are liberated by the enzyme action of the kallikrein from certain albuminous substances, the kininogenes, and which have the pharmacological activity of the kallikreins) have been utilized as anti-diabetic drugs. These kinins are oligopeptides having 9 to 11 amino acid units. The nonapeptide Brady kinin with the amino acid sequence ($NH_2$) arginine — proline- proline -glycine - phenylalanine - serine - proline - phenylalanine - arginine (COOH) and the decapeptide kallidin, extended by a lysine residue which is added to the amino end, as well as the meth-lys-Brady kinin, which is lengthened still further by the addition of a methionine residue, are substances which, when applied even in minimum quantities, have a kallikrein-like vasodilatoric effect on the circulation, will cause the relaxed muscular system to contract and will also cause vehement local pain reactions if injected subcutaneously even at minimum quantities. In this connection, see Werle, "Angewandte Chemie," (1961), pp. 689 to 720; "Arzneimittel," Volume 1, Verlag Chemie (1968), pp. 876 to 880.

It is also known from the published German patent application 2 357 507 that the kinins, such as Brady kinin and kallidin, promote the mobility of the spermatozoa, and they are therefore recommended as means to enhance fertility, for example, in artificial insemination.

The search has continued for improved anti-diabetic drug compositions which may be administered orally. This invention was made as a result of that search.

OBJECTS AND SUMMARY OF THE INVENTION

Accordingly, a general object of the present invention is to avoid or substantially alleviate the above problems of the prior art.

A more specific object of the present invention is to provide an improved anti-diabetic composition.

Another object of the present invention is to provide an anti-diabetic composition which may be administered orally.

Other objects and advantages of the invention will become apparent from the following summary and description of the preferred embodiments of the present invention.

The present invention provides an anti-diabetic drug which may be administered orally. The drug comprises a sulfonyl urea and from about 10 $\mu$ grams to about 20 milligrams of at least one kinin in retarded form per unit dosage.

DESCRIPTION OF THE PREFERRED EMBODIMENTS

It was found unexpectedly that oral anti-diabetic drugs with a basis of sulfonyl ureas have an intensified effect on the blood sugar level if they are combined with from about 10 $\mu$ grams to about 20 milligrams, and preferably from about 100 $\mu$ grams to about 1 milligram of at least one kinin in retarded form, per unit of application. Although some sulfonyl ureas have greater anti-diabetic effects than others, the substantially increased effect of the sulfonamide and the kinin allows one to reduce the conventional dosage of the sulfonyl ureas. Thus, a reduction of about one third to about one fifth of the amount of sulfonyl urea conventionally used is needed in order to obtain a similar anti-diabetic effect. For example, the use of from about 0.1 to about 1 gram of tolbutamide or from about 0.5 to about 15 milligrams of glibenclamide with from about 100 $\mu$ grams to about 1 milligram of Brady kinin will have the same blood sugar reducing effects on the patients as may be attained by conventional doses of from about 0.5 to about 1.5 grams of tolbutamide or from about 2.5 to about 20 milligrams of glibenclamine.

The kinins in this novel composition improve the effectiveness of the insulin which is liberated from the pancreas by the sulfonyl urea. The admixture of the kinin makes it possible to help those diabetics who heretofore could not regulate the blood sugar level orally and had to resort to insulin injections.

The intensifying effect of the kinins on the activity of the sulfonyl urea results in a lowering of the blood sugar level. This is surprising since it must be assumed that the kallikrein accomplishes its pharmacological effect by liberating Brady kinin and kallidin from kininogeneous albuminous substances. However, kallikrein is known to accelerate the resorption of glucose by the intestinal mucous membrane if applied orally. In this connection, see Meng et al, "Kininogenases and Kallikrein," [Schattauer, New York (1973)], pp. 75 to 80; and Moriwaki et al, "Kalinogenase and Kallikrein, " [Schattauer, New York (1975)], pp. 57 to 62. The kallikrein, or the kinins, could therefore be expected to cause the availability of a greater amount of glucose and thus an increase in the blood sugar level. Such availability of a greater amount (and thus an increase in the glucose level of the blood) which might exist even when the drug of the present invention is being administered due to the presence of the kinins at the glucose resorption from the nutritious matter by the intestinal mucous membrane, will be absorbed within the organism due to the intensification of the sulfonyl urea effect and the interconnected activation of the insulin released at the muscular tissue of the pancreas. Indeed, there is even a reduction of the glucose level within the blood. As noted hereinabove, it is known that the kallikreine has only a temporary efficacy and will cease to show any effect on the organism after being applied for several days. The composition of the present invention, however, does not display such phenomena of resistance even after an extensive continuous application of the novel oral anti-diabetic drug. Furthermore, the kinins, being oligopeptides, do not have any allergic effects which are observed especially in the case of high molecular substances, a fact which also applies to insulin.

In order to insure a longer lasting and uniform delivery of the kinin components within the stomach-intestine tract, the invention provides that the kinin component of the novel oral anti-diabetic drug is arranged in retarded form. This may be accomplished in any manner known to those skilled in this art, such as embedding the substance in carrier materials which will either slowly dissolve or not dissolve at all. Any person skilled in this art knows a great number of methods and materials which will effect such a delay in the delivery and thus of the resorption. The sulfonyl urea components may also be present in this retarded form but it is not necessary to delay their resorption. One suitable method of attaining the desired delay in the resorption of the kinin components is the use of several small drug pellets, with the active substances being placed inside carrier materials which will dissolve in the stomach-intestine tract at diverse rates and which are combined within a gelatine capsule into one complete unit.

It is also possible to attain a long-lasting continuous delivery of the active substances by embedding these substances in a porous synthetic matrix. By molding and pressing together into pills a mixture of a sulfonyl urea powder and a granulate of a not readily soluble carrier material, such as a fatty carrier material, wherein the kinin components are incorporated in the granular material, one obtains a suitable form of application for the novel oral anti-diabetic drug. The retardation should be adjusted in such a way that a delivery of the kinin is insured for a time period of from about 3 to about 8 hours in one application because the effect of the sulfonyl urea delivery will last throughout this time period. In this manner, there will be insured a uniformly intensifying effect of the kinin relative to the lowering of the glucose level within the blood as caused by the sulfonyl urea.

The novel combination of sulfonyl urea with kinin in retarded form may be administered suitably in the form of pills, capsules or tablets, such as tablets in laminated form wherein one layer contains the sulfonyl urea and the other layer contains the kinin, for example Brady kinin in retarded form.

Since the kinins may be easily prepared synthetically in the form of nona or decapeptides, the novel combination makes available an oral anti-diabetic drug which in many instances may replace the undesirable, heretofore necessary, subcutaneous injections of insulin which is costly because it must be prepared from animal organs by means of an involved process.

The reduction in the amount of sulfonyl urea necessary for each dose, made possible by the addition of the kinin, also makes possible the oral treatment of diabetes which heretofore could not be treated in such a way due to the side-effects of the oral drugs which were then available.

The present invention is further illustrated by the following examples. All parts and percentages in the examples as well as in the specification and claims are be weight unless otherwise specified.

EXAMPLE 1

Pulverized 1-butyl-3-(p-tolylsulfonyl) urea (tolbutamide) and a wax- and fat-containing retarding granulate which contains 100 milligrams of Brady kinin per 100 grams of granulated material are mixed at a weight ratio of 7:3, and this mixture is then pressed into tablets of 0.5 grams each. Thus, each tablet contains 0.35 grams of tolbutamide and 150 $\mu$ grams of Brady kinin. By using a dosage of 1 to 2 tablets in the morning and to 2 tablets at night, it is possible to keep the blood sugar of patients at the desired level.

EXAMPLE 2

As described in Example 1, a mixture is produced from pulverized 1-cyclohexyl-3-[p-(2-{5-chloro-2-methoxy-benzamido}ethyl) phenyl sulfonyl] urea (glibenclamide) and a tablet base mass (agar-agar, calcium carbonate and talcum) at a weight ratio of 1:100, and then mixed with the retarding granulate of Example 1 at a weight ratio of 7:3. The tablets weigh 0.5 grams each and contain 3.75 milligrams of glibenclamide and 150 $\mu$ grams of Brady kinin.

These tablets make it possible to maintain the blood sugar of patients at the desired level by doses of ½ to 1 or 2 tablets in the morning and of 1 to 2 tablets at night, depending on the seriousness of the diabetic illness.

Other highly effective sulfonyl ureas may be used in place of the glibenclamide. These sulfonyl ureas include, for example, glisoxepide or glybornuride in like concentrations.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of the invention.

We claim:

1. An anti-diabetic drug to be taken orally comprising a sulfonyl urea which possesses a therapeutical blood sugar reducing effect by oral application and from about 10 μ grams to about 20 milligrams of at least one kinin in retarded form per unit dosage.

2. The drug of claim 1, wherein said drug contains from about 100 μ grams to about 1 milligram of kinin.

3. The drug of claim 2 wherein said kinin is selected from the group consisting of Brady kinin and kallidin.

4. The drug of claim 1, wherein said sulfonyl urea is selected from the group consisting of tolbutamide and glibenclamide.

5. The drug of claim 2, wherein said sulfonyl urea is selected from the group consisting of tolbutamide and glibenclamide.

6. The drug of claim 4 wherein said drug contains from about 0.1 to about 1 gram of tolbutamide.

7. The drug of claim 4 wherein said drug contains from about 0.5 to about 15 milligrams of glibenclamide.

8. The drug of claim 1, wherein said sulfonyl urea is also present in retarded form.

9. The drug of claim 2 wherein said sulfonyl urea is present in retarded form.

10. In an anti-diabetic drug containing a sulfonyl urea which possesses a therapeutical blood sugar reducing effect by oral application, the improvement which comprises adding from about 10μ grams to about 20 milligrams of at least one kinin to said sulfonyl urea in order to reduce the amount of sulfonyl urea required to be effective against diabetes.

* * * * *